United States Patent [19]

Wiessner

[11] Patent Number: 5,444,169

[45] Date of Patent: Aug. 22, 1995

[54] PROCESS AND APPARATUS FOR THE SYNTHESIS OF BUTYNEDIOL

[75] Inventor: Frank Wiessner, Munich, Germany

[73] Assignee: Linde Aktiengesellschaft, Wiesbaden, Germany

[21] Appl. No.: 169,663

[22] Filed: Dec. 20, 1993

[30] Foreign Application Priority Data

Jun. 20, 1991 [DE] Germany .................. 41 20 446.8

[51] Int. Cl.⁶ .............................................. C07C 31/18
[52] U.S. Cl. ................................... 568/855; 568/856
[58] Field of Search ................................. 568/855, 856

[56] References Cited

U.S. PATENT DOCUMENTS

| | | | |
|---|---|---|---|
| 3,154,589 | 10/1964 | Moore, Jr. | 260/635 |
| 4,093,668 | 6/1978 | Reiss et al. | 568/855 |
| 4,117,248 | 2/1986 | Prater et al. | 568/855 |

OTHER PUBLICATIONS

Derwent World Patents Index, Abstract of DE 28 14 447. Dec. 1993.

*Primary Examiner*—Johann Richter
*Assistant Examiner*—Rebecca Cook
*Attorney, Agent, or Firm*—Millen, White, Zelano & Branigan

[57] ABSTRACT

The conversion of formaldehyde and acetylene in the presence of a suspension catalyst to butynediol is usually performed in a cascade of reactors, wherein the separation of the catalyst from the product solution takes place per individual reactor. This can be performed by filters installed in the reactor or by suitable filter apparatuses outside the reactor. A part of the catalyst present in the reactors can be drawn off and replaced by regenerated and/or fresh catalyst. The catalyst drawn off from the reactors can advantageously be fed to a regeneration. The replacement of the catalyst in the reactor can take place discontinuously or continuously. In the reactors of the cascade, a catalyst amount of 50–200 g, preferably of 75–125 g, per liter of reaction solution is used.

15 Claims, 1 Drawing Sheet

PROCESS AND APPARATUS FOR THE SYNTHESIS OF BUTYNEDIOL

CROSS-REFERENCE TO RELATED APPLICATION

This application is a continuation-in-part of International Application No. PCT/EP92/01376, filed Jun. 17, 1992, claiming priority of German Application P 41 20 446.8, filed Jun. 20, 1991.

1. Field of the Invention

The invention relates to a process and associated apparatus for the synthesis of butynediol from an aqueous solution containing formaldehyde by reaction with acetylene in the presence of a suspended catalyst and, in particular, wherein the solution is conveyed in a cascade through several reactors, the solution drawn off from the first to the penultimate reactor of the cascade being fed to the next reactor in the cascade, acetylene being introduced into the reactors, a butynediol-rich solution being drawn off from the last reactor in the cascade, and a butynediol-containing product stream being obtained by separation of the catalyst from the solution.

2. Background of the Invention

From DE-PS 28 14 447, U.S. Pat. No. 4,117,248 being a counterpart, a low-pressure ethynylation process is known for the production of butynediol from formaldehyde and acetylene by using a suspended, finely distributed catalyst in a cascade of reactors. Residual formaldehyde, dissolved acetylene, produced butynediol, water and the suspension catalyst are conveyed through reactors and pipes up into a separating device, where a catalyst-containing stream is separated from the product solution and then recycled to the reactor cascade. The separation of the catalyst-containing stream from the product solution takes place in the known process according to the above-mentioned patent by a pressure leaf filter.

The following disadvantages exist in the described way in which the process is performed, also when other separating devices are used:

The previously known catalysts are deactivated when the solution in contact with the catalyst contains acetylene in less than stoichiometric amounts. This fact is usually taken into account by providing excess acetylene in the reaction mixture. Nevertheless, the danger of damage to the catalyst continues, especially in the pipes and the separating device, since the catalyst settles and thus a catalyst concentration occurs at certain points.

The main disadvantage of the known process is caused by the fact that since the suspension catalyst has to be kept flowable, a considerable part of the butynediol produced in the catalyst-containing solution is recycled from the separating device to the reactor cascade. But the recycled butynediol has an inhibiting effect on the reaction.

Thus, the conversion rate achieved overall of the initial components to butynediol in the process is reduced. Furthermore, the content of residual formaldehyde in the product solution increases. But this increased residual formaldehyde content entails additional problems in the case of a further processing of the product stream, for example, in a desired hydrogenation of the butynediol from the product stream.

The danger of damage to the catalyst by acetylene deficiency decreases with decreasing temperature. The catalyst can thus be concentrated at reduced temperature. But the flowability of the solution is also reduced with decreasing temperatures, by which the filtering behavior of the solution is worsened. Thus, for example, the filtrate stream returns to approximately a quarter of the original filtrate stream when the temperature decreases from about 80° to about 20° under otherwise identical filtering conditions. As a result, when the process is performed at low temperatures, the expenditure for equipment is substantially increased.

SUMMARY OF THE INVENTION

An object of the invention is, therefore, to provide an improved process of the initially mentioned type, preferably a process which avoids the indicated disadvantages in a simple manner.

Another object is to provide an apparatus for conducting the process of the invention.

Upon further study of the specification and appended claims, further objects and advantages of this invention will become apparent to those skilled in the art.

To attain the process aspect of the invention, the separation of the catalyst from the solution takes place per individual reactor of the cascade.

According to the invention, the catalyst is retained in the individual stages of the reactor cascade; or, in other words, the catalyst does not cascade. According to one embodiment of the invention, the separation of the catalyst from the solution can be performed outside the reactors. The catalyst, after it is drawn off with the solution from the individual reactor, is separated from the latter, and again fed to the same reactor. The catalyst-free solution is introduced in the next reactor of the cascade or drawn off as product stream from the final reactor of the cascade. By recycling the catalyst in the reactor, a part of the solution drawn off from this reactor is recycled in this reactor, but this solution exhibits the same butynediol concentration, as it exists in the reactor, so that no butynediol concentration inhibiting the conversion reaction in the individual reactors occurs by the recycling as with the process according to the prior art.

The retention time of the catalyst outside the reactors is short as compared to that according to processes of the prior art. In the reactors, an excess of acetylene can be easily maintained. Thus, damage to the catalyst by acetylene deficiency therefore does not occur in the process according to the invention.

But the catalyst can also be separated from the solution according to the invention inside the reactor with special advantage. Damage to the catalyst does not occur by virtue of the acetylene excess in the reactors. A recycling of solution in the reactors does not occur in this case.

As reactors, all reactors can be used in the process according to the invention which make possible a good distribution of the reaction components and of the catalyst in the reactor. In particular, stirred vessels are suitable for this purpose. The separation of the catalyst from the solution and thus the drawing off of a catalyst-free solution from the stages of the reactor cascade can be achieved by filters, but also by other separating devices, such as, for example, hydrocyclones as a separating device outside the reactors. The separation of the catalyst from the solution takes place in the process according to the invention at reaction temperature. This is between about 60° and 100° C., preferably between 80° and 90° C. At these high temperatures, the suspension is thin, which significantly facilitates the separation. The reaction takes place at ambient pressure or at slightly increased pressure.

The conversion of the initial components to butynediol is improved if a catalyst amount of 50 g to 200 g, preferably of 75 g to 125 g, per liter of solution is present in the reactors.

In the development of the process according to the invention, a partial amount of the suspended catalyst present in the reactors of the cascade is drawn off from the reactors in addition to the catalyst-free solution and replaced by a corresponding amount of catalyst. Thus, it can be assured that the normal aging of the catalyst, particularly in continuous operation, does not lead to a decreasing conversion rate to butynediol.

The replacement of the catalyst can take place discontinuously. But the catalyst is advantageously drawn off from the reactors and fed to the latter continuously.

In further development of the process according to the invention, the catalyst drawn off from the reactors can be fed at least partially to a regeneration step, thereby permitting at least a part of the drawn-off catalyst to be profitably used again in the process.

Regenerated and/or freshly suspended catalyst is advantageously introduced in the reactors. In the way in which this process is performed according to the invention, an especially high conversion of the initial components to butynediol can be achieved. In this connection, the suspended catalyst can be conveyed to the reactors directly or with the solution. In the last-mentioned case, the catalyst is already mixed with the solution outside the reactor.

As catalysts in the process according to the invention, all suspension catalysts known for the butynediol production are suitable. Note, for example, all of the catalysts mentioned in the aforesaid DE-PS 28 14 447 corresponding to U.S. Pat. No. 4,117,248, as well as U.S. Pat. Nos. 3,154,589; 2,232,867; 2,300,969; 2,487,069; 2,712,560; 2,768,215; 3,108,140; 3,294,849; 3,560,576; and 3,920,759; and German DAS 2,206,693. As compared to results achieved with catalysts made of a copper compound on an aluminum oxide support, even better results are obtained with the catalysts employed in the invention of said DE-PS 28 14 447 corresponding to U.S. Pat. No. 4,117,248, namely, a catalyst based on magnesium silicate support, especially a finely divided cuprous acetylide supported on magnesium silicate, the catalyst optionally containing a minor amount of bismuth, as well.

The invention further relates to a device for performing the initially described process with several reactors, which are connected by connecting pipes to a cascade and respectively comprise feed pipes for the solution and for acetylene, as well as pipes for drawing off the solution and the gases that are liberated in the reactors. According to the invention, a separating device to separate a catalyst-free solution is placed in or with each reactor.

This separating device is comprised of a filter with filter candles or filter surfaces. But separating devices, such as, for example, cyclones, can also be used outside the reactor. In a separating device outside the reactor, a pipe leads from the reactor to the separating device, by which catalyst and solution are conveyed into the separating device, a pipe leads from the separating device to the reactor, by which the catalyst is recycled in the reactor, and a pipe leads from the separating device, by which catalyst-free solution is drawn off from the stage of the reactor cascade.

In a special embodiment of the device according to the invention, the reactors or the feed pipes for the solution are equipped in addition with further pipes, by which the catalyst is fed. Furthermore, a pipe leads from each reactor, by which catalyst is drawn off.

Advantageously, in a further development of the invention, the connecting pipes are equipped with pumps. Since only catalyst-free solution is conveyed from reactor to reactor by the connecting pipes, simple pumps can be used problem-free in the connecting pipes, since the danger of damage to the catalyst in the pumps does not exist.

The invention is explained in more detail below based on an embodiment.

DETAILED DESCRIPTION PREFERRED EMBODIMENTS

Figure 1:
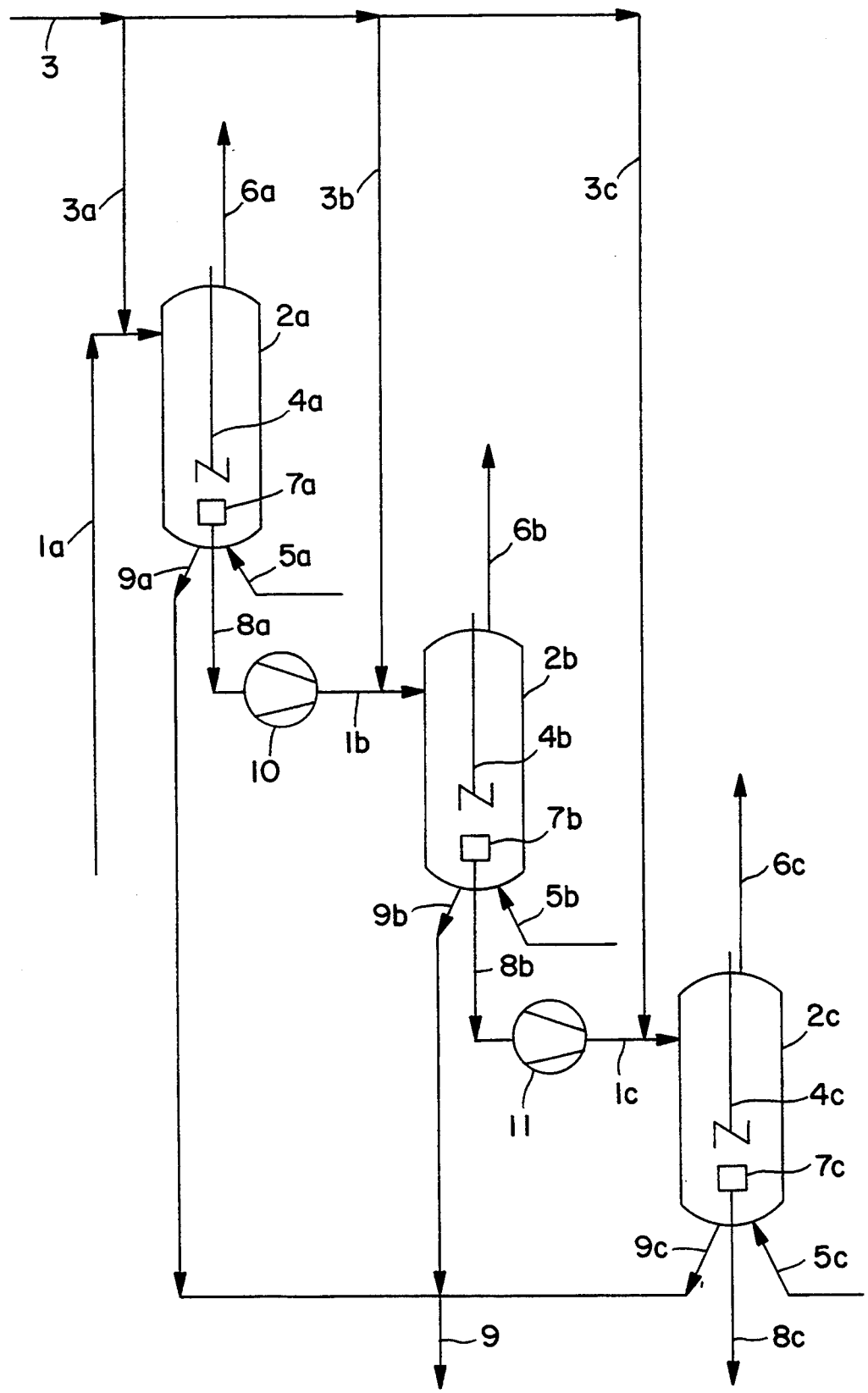
FIG. 1 is a schematic flowsheet of a reactor cascade according to the invention.

In FIG. 1, a diagram of a reactor cascade according to the invention with three stirred vessels is represented. At least formaldehyde-containing solution is conveyed in first stirred vessel 2a by pipe 1a. Suspended catalyst is also introduced in stirred vessel 2a by pipe 3 and pipe 3a. Stirred vessel 2a is equipped with stirrer 4a. Stirrer 4a assures a thorough mixing of the reaction solution. Acetylene is gassed into the reactor space by pipe 5a. A partial conversion of the formaldehyde and acetylene to butynediol takes place in the stirred vessel. Excess gases, basically acetylene, are drawn off from stirred vessel 2a by pipe 6a. In the lower area of stirred vessel 2a, a filter 7a is placed, which retains the suspended catalyst in stirred vessel 2a. Filter 7a is placed in stirred vessel 2a so that, because of the flow conditions in stirred vessel 2a, a clogging of filter 7a is avoided. By filter 7a, a reaction solution already containing butynediol is drawn off from stirred vessel 2a by pipe 8a. The reaction mixture is fed by pump 10 of the second stage of the reactor cascade. Suspended catalyst is drawn off by pipe 9a from the bottom of stirred vessel 2a.

By pipe 1b, the reaction mixture is conveyed from the first stage of the cascade to the second stage. Stirred vessel 2b forms the core of the second stage of the cascade. Stirred vessel 2b is operated corresponding to stirred vessel 2a and therefore exhibits equivalent internal fittings, feed pipes and drains. In FIG. 1, a third stage of the cascade with stirred vessel 2c also with equivalent internal fittings, feed pipes and drains, is also represented. The equivalence is illustrated in FIG. 1 by identical reference numbers, which are provided with letters a, b, or c to identify the first, second or third stage of the reactor cascade. The solution drawn off from the second stage of the cascade by pipe 8b is conveyed by pump 11 and pipe 1c to the third stage of the shown reactor cascade. In each stage of the cascade, another conversion to butynediol takes place, the number of the cascade stages used is not preset by the invention, but it depends on specific boundary conditions of a unit.

A catalyst-free, butynediol-rich product stream is obtained from the final stage of the reactor cascade, which can be further used or worked up at will in the embodiment, a butynediol-rich product stream is drawn off from stirred vessel 2c by pipe 8c.

Catalyst streams 9a, 9b or 9c conveyed from stirred vessels 2a, 2b or 2c can be fed by pipe 9 to a regeneration not represented in FIG. 1. The catalyst suspension obtained in the regeneration can be profitably recycled in the process by pipe 3.

Overall, the advantages of the process according to the invention or of the device according to the invention can be summarized as follows: The reactors, especially the stirred vessels, can be made significantly smaller with the same butynediol conversion. Thus, the entire stirrer and gassing system can also be made of significantly smaller dimensions. The separation of the catalyst suspension from the solution takes place by a simple separating device, for example, by simple, conventional filters. Moreover, the filtering conditions are especially advantageous because of the high temperatures and the flow conditions. Furthermore, the process according to the invention or the device according to the invention prevents irreversible damage to the suspension catalyst. Still further, the fail-safe operation of a unit for butynediol production is significantly improved by the invention.

The entire disclosures of all applications, patents, and publications, cited above and below, and of corresponding German Application P 41 20 446.8, filed Jun. 20, 1991, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

We claim

1. In a process for the synthesis of butynediol from an aqueous solution containing formaldehyde by reaction of said formaldehyde with acetylene in the presence of a suspended catalyst, wherein the solution is conveyed in a cascade by several reactors, the solution drawn off from the first through the penultimate reactor of the cascade being fed to the next reactor in the cascade, and acetylene being introduced into each of the reactors, and a butynediol-rich solution being drawn off only from the last reactor in the cascade, the improvement which comprises separating the catalyst from the solution in each individual reactor of the cascade above the last reactor so as to prevent the catalyst from cascading with the solution.

2. A process according to claim 1, wherein a catalyst amount of 50 to 200 g per liter of solution is contained in each of the reactors.

3. A process according to claim 1, wherein a partial amount of the catalyst present in each reactor of the cascade is drawn off and a corresponding amount of non-spent catalyst is fed to each reactor.

4. A process according to claim 3, wherein catalyst is drawn off and fed continuously.

5. A process according to claim 3, wherein the catalyst drawn off from the reactor is fed at least partially to a regeneration stage.

6. A process according to claim 3, wherein at least one of regenerated and fresh catalyst is used as catalyst introduced in the reactors.

7. A process according to claim 1, wherein the catalyst consists essentially of a copper compound on a magnesium silicate support.

8. A process according to claim 2, wherein the catalyst amount is 75–125 g per liter of solution.

9. A process according to claim 2, wherein a partial amount of the catalyst present in each reactor of the cascade is drawn off and a corresponding amount of non-spent catalyst is fed to each reactor.

10. A process according to claim 4, wherein the catalyst drawn off from the reactor is fed at least partially to a regeneration stage.

11. A process according to claim 2, wherein the catalyst consists essentially of a copper compound on a magnesium silicate support.

12. A process according to claim 8, wherein the catalyst consists essentially of a copper compound on a magnesium silicate support.

13. A process according to claim 1, wherein at least one of regenerated and fresh catalyst is used as catalyst introduced in the reactors.

14. A process according to claim 1, wherein the catalyst is separated from the solution through a filter inside each of the reactors.

15. A process according to claim 1, wherein the catalyst is separated from the solution outside each of the reactors.

* * * * *